(12) United States Patent
Buck

(10) Patent No.: US 7,658,826 B2
(45) Date of Patent: *Feb. 9, 2010

(54) REFERENCE ELECTRODE

(75) Inventor: Michael D. Buck, Berthoud, CO (US)

(73) Assignee: Hach Company, Loveland, CO (US)

( * ) Notice: Subject to any disclaimer, the term of this patent is extended or adjusted under 35 U.S.C. 154(b) by 718 days.

This patent is subject to a terminal disclaimer.

(21) Appl. No.: 11/070,329

(22) Filed: Mar. 1, 2005

(65) Prior Publication Data

US 2005/0191429 A1    Sep. 1, 2005

Related U.S. Application Data

(60) Provisional application No. 60/548,981, filed on Mar. 1, 2004, provisional application No. 60/548,982, filed on Mar. 1, 2004.

(51) Int. Cl.
    *G01N 27/26* (2006.01)
(52) U.S. Cl. .................. 204/435; 204/433; 204/416
(58) Field of Classification Search .......... 204/433–435
    See application file for complete search history.

(56) References Cited

U.S. PATENT DOCUMENTS

| | | | |
|---|---|---|---|
| 4,214,968 A * | 7/1980 | Battaglia et al. ............. 204/418 |
| 4,528,085 A * | 7/1985 | Kitajima et al. ............. 204/416 |
| 4,933,048 A | 6/1990 | Lauks et al. | |
| 4,995,960 A | 2/1991 | Wiles et al. | |
| 5,360,529 A * | 11/1994 | Edwards et al. ............. 204/435 |
| 5,421,983 A * | 6/1995 | Slack et al. ............. 204/403.06 |
| 2001/0032785 A1* | 10/2001 | Cha et al. .................... 204/435 |
| 2002/0134679 A1* | 9/2002 | Terashima et al. .......... 204/435 |

FOREIGN PATENT DOCUMENTS

WO    WO 00/58720    * 10/2000

OTHER PUBLICATIONS

Johnson C. S. et al., "Reference Electrodes for Solid Polymer Electrolytes", Extended Abstracts, Electrochemical Society, Princeton, NJ, US, vol. 93/2, Oct. 10, 1993, pp. 66-67.
Yoon H. J. et al., "Solid-state ion sensors with a liquid junction-free polymer membrane-based reference electrode for blood analysis" Sensors and Actuators B, Elsevier Sequoia S.A., Lausanne, CH, vol. 64, No. 1-3, Jun. 2000, pp. 8-14.

(Continued)

*Primary Examiner*—Nam X Nguyen
*Assistant Examiner*—Bach T Dinh
(74) *Attorney, Agent, or Firm*—Samuel M. Freund; Cochran Freund & Young LLC

(57) ABSTRACT

A reference electrode including a water-impermeable, nonconductive substrate having a surface; an electrically conductive metal/metal salt mixture layer in contact with the surface; a water-soluble alkali metal salt layer; and a water-impermeable barrier layer overlaying a portion of the alkali metal salt layer and a portion of the metal/metal salt layer, and a method for preparing same are described. When the reference electrode is placed in a water sample to be tested, water enters the exposed portion of the alkali metal salt layer where it dissolves the salt forming a saturated solution in the region of contact between the alkali metal salt layer and the metal/metal salt layer.

1 Claim, 5 Drawing Sheets

OTHER PUBLICATIONS

Eine, K. et al, "Towards a solid state reference elctrode", Sensors and Actuators B., Elsevier Sequoia S.A., Lausanne, CH, vol. 44, No. 1-3, Oct. 1997, pp. 381-388.

Bakker E, "Hydrophobic Membranes as Liquid Junction-Free Reference Elctrodes", Electroannalysis, VHC Publishers, Inc., US, vol. 11, No. 10-11, Jul. 1999, pp. 788-792.

A. Mroz et al. "Disposable Reference Electrode" Analyst vol. 123, pp. 1373-1376 (1998).

Hyuk Jin Lee et al. "Solvent-Processible Polymer Membrane-Based Liquid Junction-Free Reference Electrode" Anal. Chem. 70, pp. 3377-3383 (1998).

* cited by examiner

REFERENCE ELECTRODE

RELATED CASES

The present patent application claims the benefit of Provisional Patent Application Ser. No. 60/548,981 filed on Mar. 1, 2004 entitled "Ion-Selective Electrodes" by Michael D. Buck, also known as Mike Buck; Provisional Patent Application No. 60/548,982 filed on Mar. 1, 2004 entitled "Reference Electrode" by Michael D. Buck, also known as Mike Buck; and U.S. patent application Ser. No. 11/070,300 filed on Mar. 1, 2005 for "Ion-Selective Electrodes" by Michael D. Buck, said applications being hereby incorporated by reference herein for all that they disclose and teach.

FIELD OF THE INVENTION

The present invention relates generally to reference electrodes for use in combination with a sensor electrode to qualitatively and/or quantitatively determine the presence of a selected ion in a liquid medium using potentiometric analysis and, more particularly, to a rapidly equilibrated reference electrode which does not require internal water-based electrolytes.

BACKGROUND OF THE INVENTION

Reference electrodes are used in potentiometric analysis of qualitative and/or quantitative analyses of ions in solution. There are a variety of such electrodes, utilizing different electrode chemistry, including silver/silver chloride, calomel, and mercury/mercurous sulfate electrodes, as examples. Generally, such reference electrodes use internal aqueous electrolyte solutions and are designed and intended for long-term, repeated use.

A liquid junction-free reference electrode system is described in "Solvent-Processible Polymer Membrane-Based Liquid Junction-Free Reference Electrode," by Hyuk Jin Lee et al., Anal. Chem. 70, pages 3377-3383 (1998). Therein, the authors describe the use of solvent-processible polymer membranes for forming liquid junction-free reference electrodes in a planar solid-state format. A polyurethane matrix reference site was formed on an aluminum oxide onto which silver electrodes were printed by incorporating both cation- and anion-exchange sites (for example, potassium tetrakis(p-chlorophenyl)borate and tridodecylmethylammonium chloride) into a polyurethane matrix, and dispensing (screen-printing) a small volume of this material, typically 5 µL, onto the silver electrode and the surrounding dielectric layer. The sensors were dried in ambient air for 12 h.

In "Disposable Reference Electrode" by A. Mroz et al., Analyst 123, pages 1373-1376 (1998), the authors describe a disposable reference electrode which includes an Ag/AgCl electrode without a diaphragm, where an internal electrolyte KCl aqueous solution is enclosed in a glass-fiber filter medium in contact with a screen-printed Ag/AgCl strip conductor. The lower part of the electrode is cut open before the electrode is used.

Accordingly, it is an object of the present invention to provide stable reference electrodes which do not require calibration.

Another object of the invention is to provide inexpensive, disposable and stable reference electrodes which do not require calibration.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the reference electrode hereof includes: a water-impermeable, non-conductive substrate having a surface; an electrically conductive metal/metal salt layer disposed on the surface of the substrate; a water-soluble alkali metal salt layer disposed on the surface of the substrate and in contact with at least a portion of the metal/metal salt layer; and a water-impermeable barrier layer overlaying a portion of the alkali metal salt layer, and a portion of the metal/metal salt layer.

In another aspect of the invention and in accordance with its objects and purposes, the method for generating a reference electrode hereof includes the steps of: forming an electrically conductive metal/metal salt layer on the surface of a water-impermeable, non-conductive substrate; forming a water-soluble alkali metal salt layer on the surface of the substrate and in contact with at least a portion of the metal/metal salt layer; and overlaying a portion of the alkali metal salt layer, and a portion of the metal/metal salt layer with a water-impermeable barrier layer.

Benefits and advantages of the present invention include, but are not limited to, a stable, inexpensive, disposable reference electrode which does not require calibration.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DETAILED DESCRIPTION

Briefly, the present invention includes a stable, inexpensive, disposable reference electrode having no internal aqueous electrolyte solution, and a method for preparing same. The reference electrode is thin, compact and easy to use, and may comprise: a water-impermeable, non-conductive substrate having a surface; an electrically conductive metal/metal salt mixture layer disposed on the surface; a water-soluble alkali metal salt layer, wherein the anion of the alkali metal salt is the same as the anion of the metal salt in the metal/metal salt; and a water-impermeable barrier layer overlaying a portion of the alkali metal salt layer and a portion of the metal/ metal salt layer, wherein at least a portion of the alkali metal salt layer remains exposed. When the reference electrode is placed in an aqueous sample to be tested, water enters the exposed portion of the second layer where it dissolves the alkali metal salt. As the water proceeds toward the metal/ metal salt layer, the alkali metal salt becomes more concentrated in the solution. Upon reaching the metal/metal halide layer, the solution is saturated with the alkali metal salt. It is believed by the present inventor that the salt layer takes up or imbibes water from the solution to be investigated by capillary action. The metal salt in the metal/metal salt layer is substantially insoluble.

The metal/metal salt layer and salt layers may be screen printed or stenciled onto the supporting substrate, but other procedures are anticipated. The mask or barrier layer covering the metal/metal salt layer and the salt layer may include pressure-sensitive adhesive tape, although other barrier layers such as thermoplastic polymers, as examples, should provide the required properties. A portion of the metal/metal salt layer is exposed such that an electrical connection may be made thereto for achieving measurements of the electric potential of the reference electrode.

The reference electrode is intended for use with ion-selective electrodes disposed either on the same substrate therewith or otherwise located in a solution of ions, the concentration of which is intended to be determined by potentiometric measurements.

A generally planar surface for the substrate has been found to be suitable for the practice of the present invention.

Figure 1:
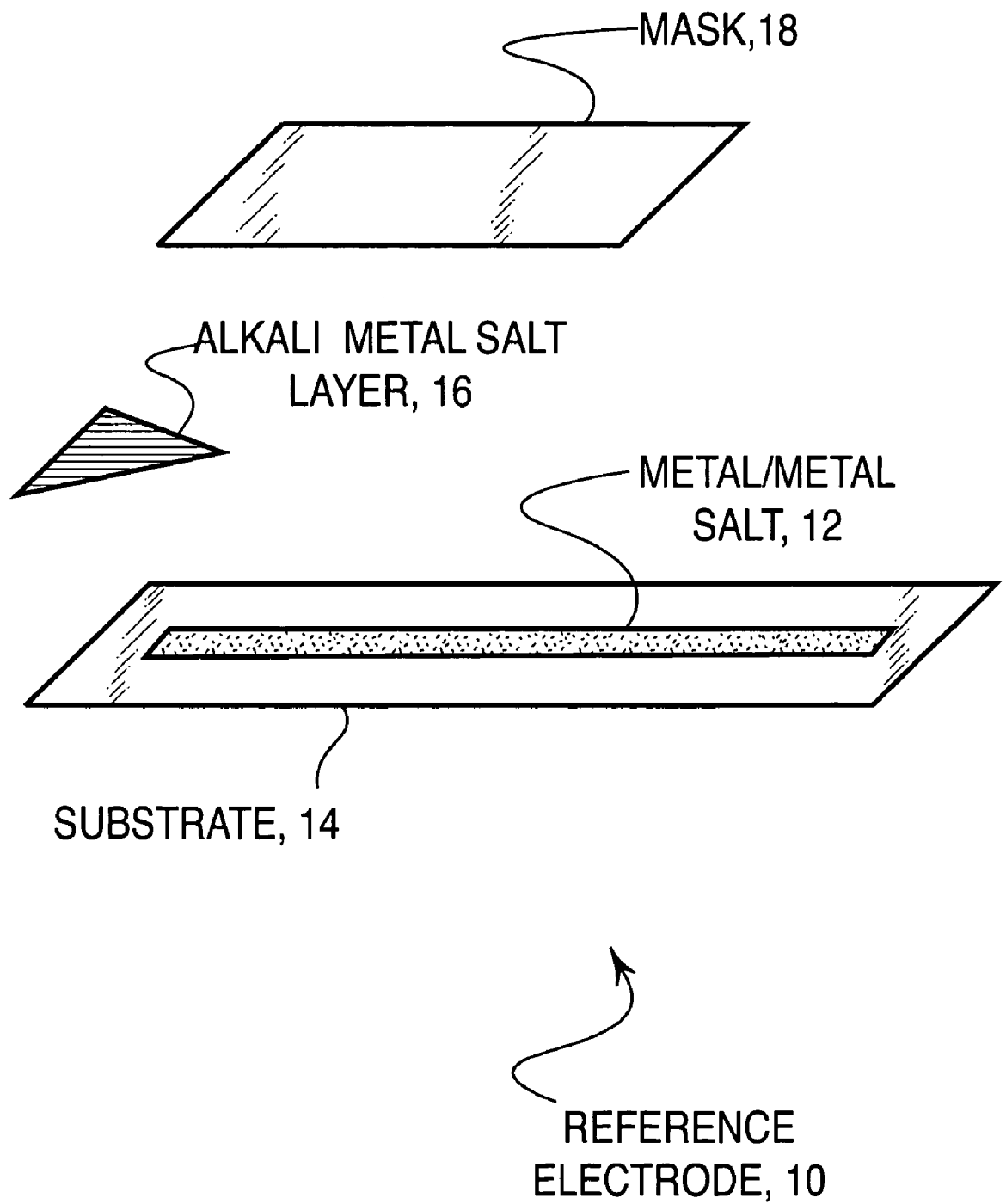
FIG. 1 is an exploded schematic representation of one embodiment of the reference electrode of the present invention.

Reference will now be made in detail to the present preferred embodiments of the invention examples of which are illustrated in the accompanying FIGURES. Similar or identical structure is identified using identical callouts. Turning now to FIG. 1, an exploded schematic representation of one embodiment of the reference electrode, 10, of the present invention is shown. Electrically conductive layer, 12, which includes a metal/metal salt mixture in a binder, is formed on the generally planar surface of water-impermeable, non-conductive substrate, 14. The metal/metal salt mixture may be silver/silver chloride, silver/silver bromide or silver/silver iodide, as examples. The binder may be a plastic material such as polystyrene or polyester, as examples. Substrate 14 may be flexible or rigid. A flexible plastic strip may be used. A ceramic strip may also be used.

Alkali metal salt layer, 16, is also formed on substrate 14 in contact with metal/metal salt layer 12. The anion of the alkali metal salt may be the same as the anion in conductive layer 12. The alkali metal salt may be KCl, KBr or KI, as examples.

Water impermeable barrier, 18, overlays alkali metal salt layer 16 and a portion of metal/metal salt layer 12 such that when reference electrode 10 is placed into a water sample, water may enter the second layer through opening, 20, between barrier 18 and substrate 14, by means of capillary action. The barrier layer may be an adhesive tape or a thermoplastic polymer, as examples.

Length, 22, of alkali metal salt layer 16 is chosen such that water being imbibed or taken up by the layer becomes saturated with the alkali metal salt present in the second layer in the vicinity of metal/metal salt layer 12 (4 mm was the length chosen for the present reference electrodes, but the invention should not be limited to this value). Electrodes having overlap, 24, of metal salt layer 16 with metal/metal salt layer 12 have been prepared and successfully tested (between about 0.02 mm and 1 mm, as an example). It is believed, however, that depending on the thicknesses of layers 12 and 16, the present reference electrode would function if the ends of the two layers were merely in contact, as opposed to overlapping. Alkali metal salt layer 16 may include a material such as diatomaceous earth to provide porosity and to provide some thickness to the layer. Layer 16 is prepared to be of a consistency such that it may be printed onto substrate 14 by screen printing, stenciling or other suitable coating processes. A water-soluble binder has been found to be necessary in order to establish a robust deposited layer after drying. Polyethylene oxide is an example of a suitable binder.

Figure 2:
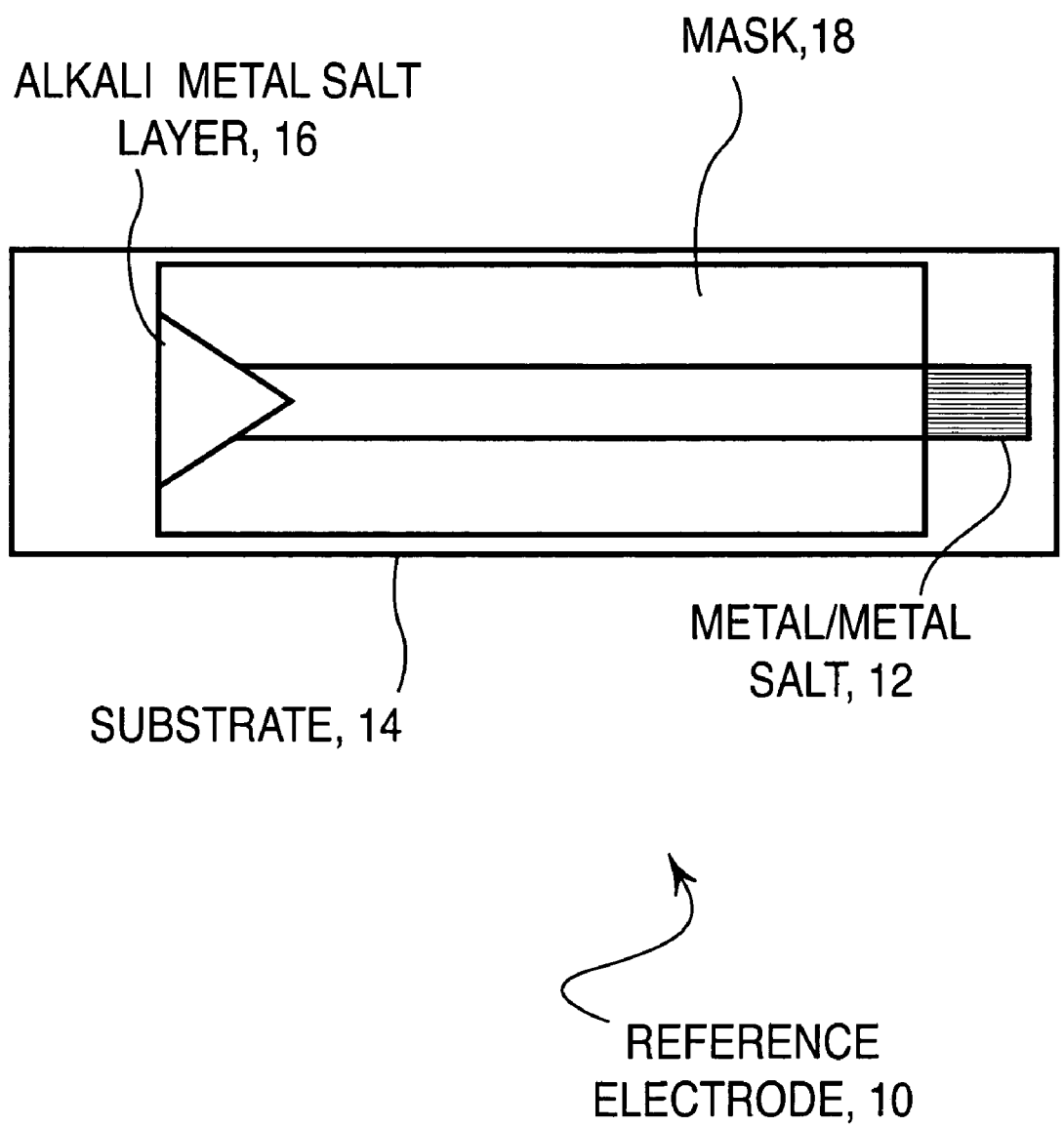
FIG. 2 is a schematic representation of a top view of the assembled reference electrode illustrated in FIG. 1 hereof.
Figure 3:
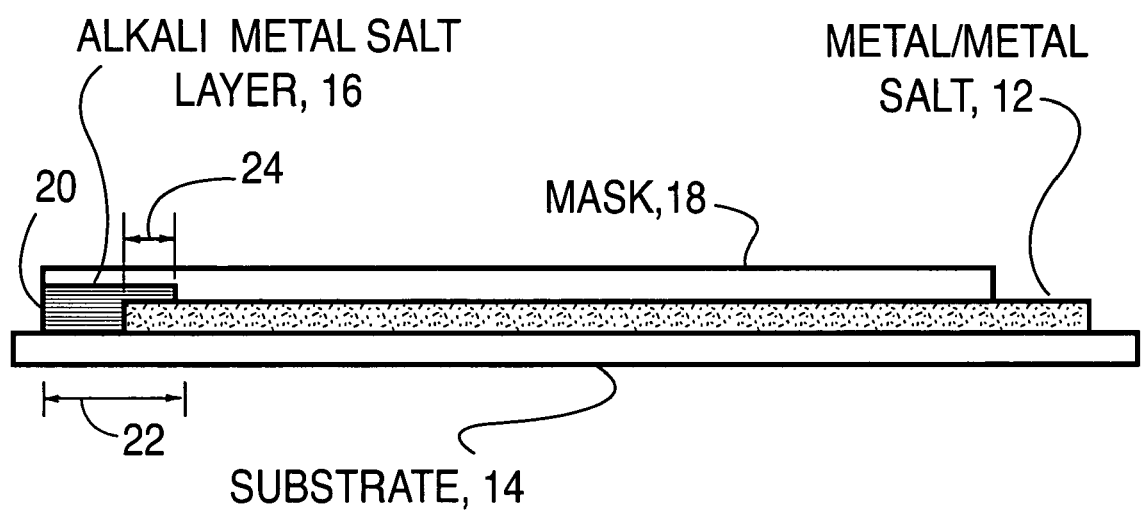
FIG. 3 is schematic representation of a side view of the assembled reference electrode illustrated in FIG. 1 hereof.

FIGS. 1-3 hereof illustrate the geometry of the alkali metal salt layer as being generally triangular; however, any geometry may be used as long as the solution is saturated with the alkali metal salt in the region of overlap 24 with metal/metal salt layer 12 when the electrode is in use.

As will be seen hereinbelow, after about 30 s of being placed in an aqueous solution of the ions to be measured, the reference electrode of the present invention will substantially reach its equilibrium potential. Moreover, the electrode is quite stable in that it will remain at substantially the same potential for an extended period (more than 1 h, as an example).

Having generally described the invention, the following EXAMPLE provides more specific details of layer formulations for two ion-selective electrodes.

EXAMPLE

One embodiment of the reference electrode of the present invention may be prepared as follows:

(1) Ag/AgCl Layer:

A solvent mixture having the approximate ratios of 37:42:11:10 by volume of Cyclohexanol (370 mL); Di(propylene glycol)methyl ether acetate (420 mL); γ-butyrolactone (110 mL); 1,2,3,4-tetrahydronaphthalene (Tetralin) (100 mL), hereinafter known as the First Solvent, is prepared. Cyclohexanone may be used in place of cyclohexanol.

(a) 15% Polystyrene in Solution in Solvent:

About 75 g of Polystyrene (melt index 14) is added to approximately 425 g of First Solvent, and the mixture heated to near reflux temperature with vigorous stirring heat the mixture to near reflux temperature for several hours to fully dissolve the polystyrene pellets.

(b) Ag/AgCl Powder:

About 70 g of commercially available mechanically flattened Technic type 235 silver flakes is dispersed in about 300 mL of methanol with stirring for approximately 20 min. to achieve substantial wetting of the silver. About 36 g of $AgNO_3$ is dissolved in approximately 200 mL of distilled water, and the resulting solution is added to the suspension of silver flakes. Approximately 16 g of KCl is dissolved in about 100 mL of distilled water, and the resulting solution is slowly added to the $Ag/AgNO_3$ mixture with vigorous stirring. The mixture was found to become thick and difficult to stir. Stirring is continued for about 15 min. after the addition of the KCl. The mixture is filtered to remove the product, and the filtered product washed with about 2 L of water in small portions to remove the $KNO_3$ present. The resulting washed product is further washed with approximately 500 mL of Methanol to remove the bulk of the water, and the methanol-washed product vacuum dried. Oven drying has been found to create lumps that are difficult to process into the finished printable suspension. The yield is between 99 g and 100 g.

(c) Ag/AgCl Suspension:

About 50 g of the 15% Polystyrene solution in the First Solvent, about 10 g of First Solvent, approximately 0.3 mL of BYK 065 defoamer, and about 1.6 mL of BYK 202 dispersing additive are added to approximately 100 g Ag/AgCl powder, and the mixture stirred to wet the powder. The resulting mixture is rolled twice in a roll mill having the feed rolls about 0.00005 in. apart, and the final viscosity of the mixture is adjusted for achieve the desired layer characteristics by adding First Solvent as required. It should be mentioned that BYK 065 and BYK 202 are commercially available additives for inks and paints, and the like. BYK 065 is a solution of polysiloxanes used for preventing foam and bubble formation, and BYK 202 is a solution of an alkylammonium salt of a polycarboxylic acid for control of flocculation, wetting and dispersing of materials such as pigments in inks and paints, and the like. There are many such products available as would be known to those skilled in the art of inks and paints.

(2) Alkali Metal Salt Layer:

(a) 5% PEO 300 k Solution:

A solvent mixture having the approximate ratios of 15:45:40 by volume is prepared by mixing 15 mL of Acetophenone, 45 mL of Benzyl alcohol, and 40 mL of p-Cymene, this solvent mixture being hereinafter referred to as the Second Solvent. About 25 g of Poly(ethylene oxide) (PEO, Avg. M.W. 300,000) is added to approximately 475 g of Second Solvent with vigorous stirring. After the solid has been added, the mixture is heated without refluxing to dissolve the PEO. The resulting solution is examined for undissolved polymer material.

(b) Alkali Metal Salt Suspension:

About 15 g of KCl (milled to pass 320 mesh), approximately 15 g of HyFlo Supercel from Celite Corp., and about 30 g of 5% PEO 300 k in the Second Solvent are stirred together to wet the powder. The resulting mixture is passed once through a three roll mill having 0.00005" roll spacing. The mixture is thinned to a thick paste with the Second Solvent as required. Overthinning will result in an suspension deposit that will be too thin and have insufficient strength. Passing the mixture through the mill more than one time has been found to result in an alkali metal salt layer that is too compact, which yields slow electrodes. The HyFlo Supercel is a diatomite filter aid.

The Ag/AgCl suspension was printed onto the upper surface of a flexible plastic strip as a substrate, and dried for approximately 8 h under reduced pressure. The resulting layer thickness was about 0.01 mm, after the dried, approximately 0.02 mm layer was pressed to reduce layer resistance (by about a factor of 3). The alkali metal salt layer (KCl) was coated onto the substrate with a portion thereof overlapping the Ag/AgCl layer, followed by drying. Resulting layer thicknesses were between about 0.05 and 1 mm. The mask or barrier layer was then applied to the Ag/AgCl and KCl layers.

Figure 4:
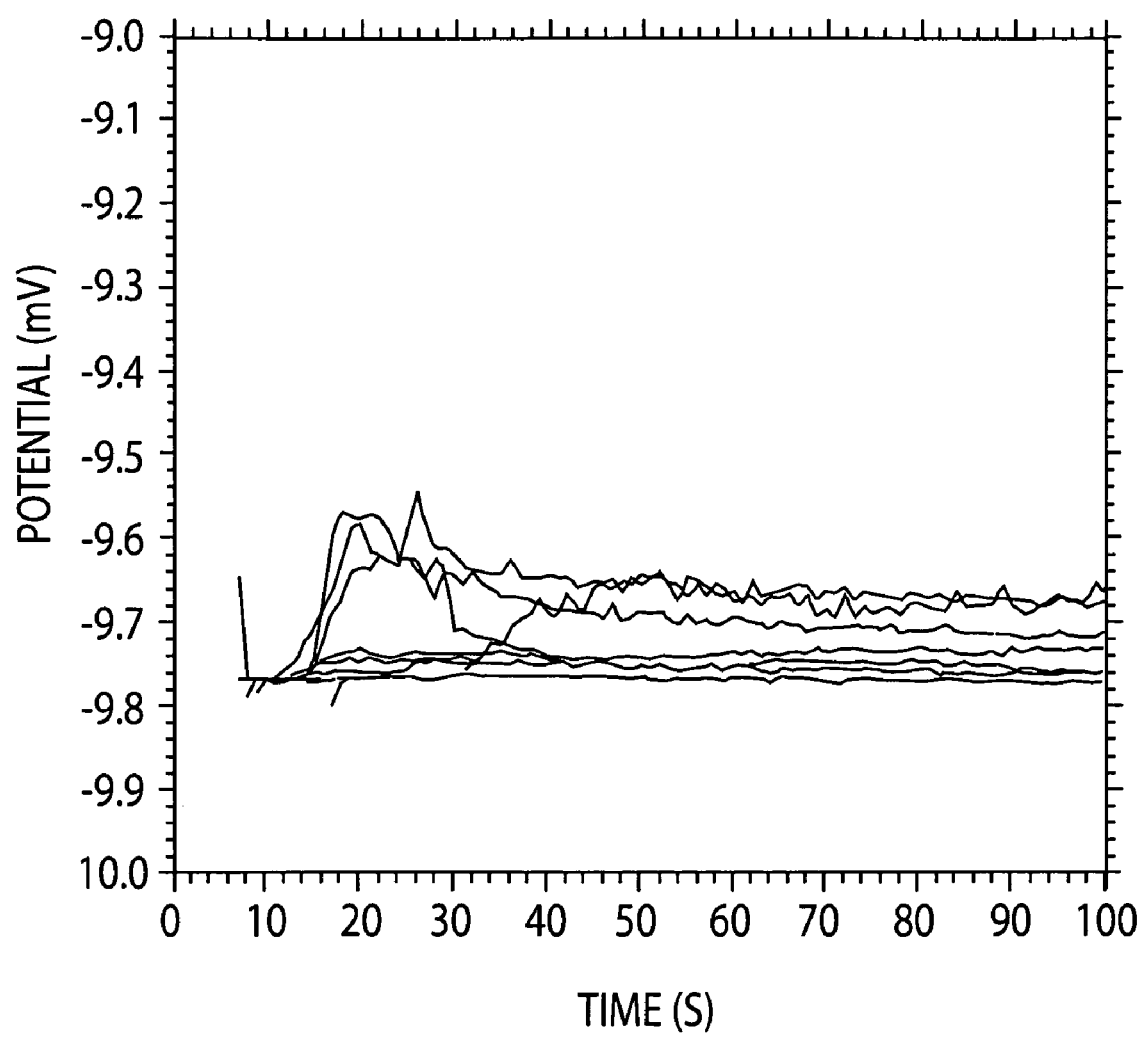
FIG. 4 is a graph of the measured electrical potentials for several reference electrodes prepared in accordance with the teachings of the present invention when compared with a commercially available reference electrode, as a function of time, illustrating the time for the electrode to reach an equilibrium potential.

FIG. 4 is a graph of the measured electrical potentials for several reference electrodes prepared as described hereinabove when compared with a commercially available Orion Sleeve Junction Ag/AgCl reference electrode, as a function of time, illustrating the time for the electrode to reach an equilibrium potential. Note that the measured potential differs by less than 0.17 mV among the 10 electrodes after 30 s of immersion. More recent data for reference electrodes fabricated in accordance with the present invention illustrates substantially the same time to reach equilibrium, but a measured electrical potential closer to zero when compared with commercial Ag/AgCl reference electrodes.

Figure 5:
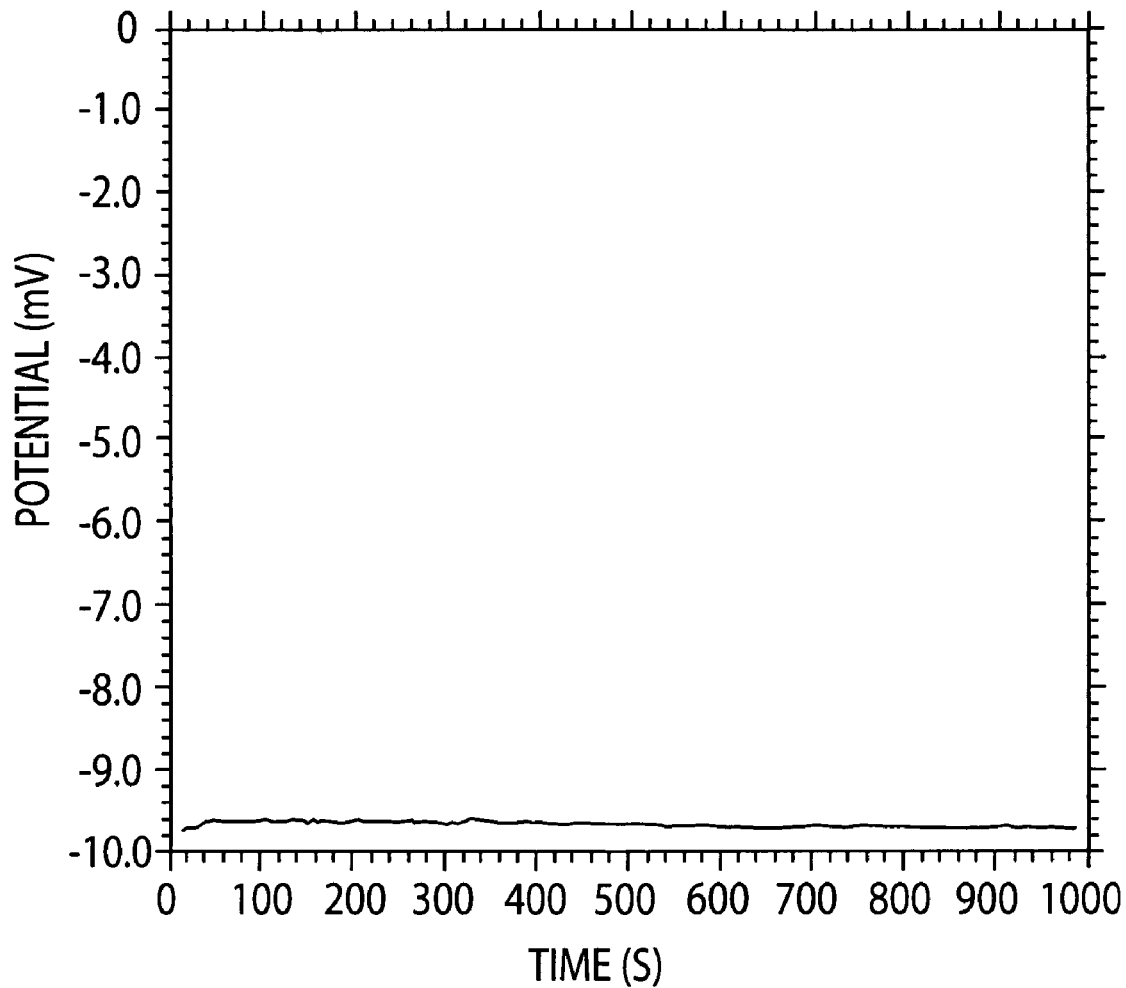
FIG. 5 is a graph of the measured electrical potential of a reference electrode prepared in accordance with the teachings of the present invention when compared with a commercially available reference electrode, as a function of time, illustrating the stability of the present reference electrode.

FIG. 5 is a graph of the measured electrical potential of a reference electrode prepared as described hereinabove, when compared with a commercially available reference electrode, as a function of time, illustrating the stability of the present reference electrode. The total drift of the electrode between about 30 s and 1000 s is less than 0.03 mV.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A reference electrode comprising in combination:
   (a) a water-impermeable, non-conductive substrate having a surface;
   (b) an electrically conductive metal/metal salt mixture layer disposed on the surface of said substrate;
   (c) a triangular dry, water-soluble alkali metal salt layer disposed on the surface of said substrate, an apex thereof overlapping and in contact with at least a portion of said metal/metal salt mixture layer; and
   (d) a water-impermeable barrier layer overlaying a portion of said triangular dry, water-soluble alkali metal salt layer, and a portion of said metal/metal salt mixture layer.

* * * * *